(12) United States Patent
Amthor et al.

(10) Patent No.: US 10,537,748 B2
(45) Date of Patent: Jan. 21, 2020

(54) COMBINED BRACHYTHERAPY AND ELECTROCHEMOTHERAPY CATHETERS

(71) Applicant: KONINKLIJKE PHILIPS N.V., Eindhoven (NL)

(72) Inventors: Thomas Erik Amthor, Hamburg (DE); Sascha Krueger, Hamburg (DE); Steffen Weiss, Hamburg (DE); Falk Uhlemann, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 541 days.

(21) Appl. No.: 14/416,451

(22) PCT Filed: Jul. 23, 2013

(86) PCT No.: PCT/IB2013/056019
§ 371 (c)(1),
(2) Date: Jan. 22, 2015

(87) PCT Pub. No.: WO2014/016762
PCT Pub. Date: Jan. 30, 2014

(65) Prior Publication Data
US 2015/0174427 A1  Jun. 25, 2015

Related U.S. Application Data

(60) Provisional application No. 61/674,411, filed on Jul. 23, 2012.

(51) Int. Cl.
*A61N 5/10* (2006.01)
*A61B 18/14* (2006.01)
(Continued)

(52) U.S. Cl.
CPC ........ *A61N 5/1007* (2013.01); *A61B 18/1492* (2013.01); *A61B 34/10* (2016.02);
(Continued)

(58) Field of Classification Search
CPC ... A61N 1/30; A61N 5/10; A61N 1/32; A61N 5/1007; A61N 1/327; A61N 2005/1008;
(Continued)

(56) References Cited

U.S. PATENT DOCUMENTS 3,078,850 A  2/1963 Schein et al.
5,458,597 A * 10/1995 Edwards et al. ............ 606/41
(Continued)

FOREIGN PATENT DOCUMENTS

CN  1586659 A   3/2005
JP  H10277163 A  10/1998

OTHER PUBLICATIONS

Damijan Miklavcic et al; "Towards Treatment Planning and Treatment of Deep-Seated Solid Tumors BYl Electrochemotherapy", Biomedical Engineering Online, 2010, pp. 1-12.
(Continued)

*Primary Examiner* — Catherine M Voorhees
*Assistant Examiner* — Roland Dinga (57) ABSTRACT

A medical device for multiple treatment therapies includes a hollow tube (102) having a first end portion with an electrode (104) disposed at the first end portion and an insulator (108) configured over a length of the tube such that conductive materials of the tube, except for the electrode, are electrically isolated from an exterior surface the tube. A conductive connection (127) is configured to electrically couple to the electrode to provide a voltage thereto. A selectively closeable valve (106) is configured to dispense a medical fluid from the tube.

15 Claims, 5 Drawing Sheets (51) Int. Cl.
*A61N 1/05* (2006.01)
*A61N 1/20* (2006.01)
*A61N 1/32* (2006.01)
*A61M 39/22* (2006.01)
*A61B 34/00* (2016.01)
*A61B 34/10* (2016.01)
*A61B 90/00* (2016.01)
*A61B 18/00* (2006.01)

(52) U.S. Cl.
CPC .............. *A61B 34/25* (2016.02); *A61B 90/37* (2016.02); *A61M 39/22* (2013.01); *A61N 1/0502* (2013.01); *A61N 1/205* (2013.01); *A61N 1/327* (2013.01); *A61N 5/1002* (2013.01); *A61N 5/1027* (2013.01); *A61B 2018/00107* (2013.01); *A61B 2018/00577* (2013.01); *A61B 2018/00613* (2013.01); *A61B 2018/00994* (2013.01); *A61B 2018/143* (2013.01); *A61B 2018/1472* (2013.01); *A61B 2090/374* (2016.02); *A61B 2090/376* (2016.02); *A61B 2090/378* (2016.02); *A61B 2090/3762* (2016.02); *A61N 2005/1008* (2013.01); *A61N 2005/1021* (2013.01); *A61N 2005/1024* (2013.01)

(58) Field of Classification Search
CPC ........... A61N 2005/1024; A61B 17/39; A61B 18/14; A61B 18/1492; A61B 201/00577; A61M 39/22; A61M 39/23

USPC ... 607/96, 98–102, 104, 115, 116, 120, 154; 606/41, 45–50; 604/20, 21–22, 116–117
See application file for complete search history.

(56) References Cited

U.S. PATENT DOCUMENTS

| | | | |
|---|---|---|---|
| 6,032,061 A * | 2/2000 | Koblish | A61L 29/085 600/372 |
| 6,428,504 B1 | 8/2002 | Riaziat et al. | |
| 6,723,094 B1 | 4/2004 | Desinger | |
| 7,160,296 B2 | 1/2007 | Pearson et al. | |
| 7,517,347 B2 | 4/2009 | Hug et al. | |
| 8,024,048 B2 | 9/2011 | Schroeppel et al. | |
| 2005/0004507 A1* | 1/2005 | Schroeppel et al. | 604/20 |
| 2005/0049542 A1* | 3/2005 | Sigg et al. | 604/20 |
| 2006/0112343 A1 | 5/2006 | Ducheneaut et al. | |
| 2007/0112342 A1* | 5/2007 | Pearson et al. | 606/34 |
| 2007/0135881 A1* | 6/2007 | Vilims | 607/117 |
| 2008/0071264 A1 | 3/2008 | Azure | |
| 2009/0118732 A1* | 5/2009 | Desinger | 606/49 |
| 2015/0174427 A1 | 6/2015 | Amthor et al. | |

OTHER PUBLICATIONS

G. Sersa et al; "Electrochemotherapy in Treatment of Tumours", Science Direct, EJSO The Journal of Cancer Surgery, vol. 34, 2008, pp. 232-240.

Forde, P.F. et al., "Minimally invasive intraluminal tumor ablation". Clinical Aspects of Electroporation, 2011, Part 2, 137-141. Abstract.

* cited by examiner

COMBINED BRACHYTHERAPY AND ELECTROCHEMOTHERAPY CATHETERS

This application is a national stage application under 35 U.S.C. § 371 of International Application No. PCT/IB2013/056019 filed on Jul. 23, 2013 and published in the English language on Jan. 30, 2014 as International Publication No. WO 2014/016762 A1, which claims priority to U.S. Application No. 61/674,411 filed on Jul. 23, 2012, the entire disclosures of which are incorporated herein by reference.

This disclosure relates to medical instruments and more particularly to multi-function instruments for providing different therapies in a same interventional procedure.

Electrochemotherapy is a relatively new local tumor therapy employing the technique of cell electroporation. An electric field is generated in a tumor region between a set of electrodes. This electric field makes the cell membranes permeable to large molecules for a short time, thereby allowing anticancer drugs to enter the cells. This form of therapy may be employed for treating cutaneous and subcutaneous tumors. Considering the increasing availability of modern image-guidance techniques, it is most probable that this kind of therapy will be used for treating all kinds of tumors even deep inside the body. Electrochemotherapy is not specific to certain types of tumors.

Brachytherapy and especially high dose rate (HDR) brachytherapy is another very effective local/focal tumor therapy. In HDR brachytherapy, small radioactive sources are temporarily (on the order of minutes) inserted directly into the tumor through one or several catheters ("applicators"). The delivery catheters typically remain in the patient's body over several such treatment sessions.

In accordance with the principles of the present invention, a medical device is provided for multiple treatment therapies which includes a hollow tube having a first end portion with an electrode disposed at the first end portion and an insulator configured over a length of the tube such that conductive materials of the tube, except for the electrode, are electrically isolated from an exterior surface the tube. A conductive connection is configured to electrically couple to the electrode to provide a voltage thereto. A selectively closeable valve is configured to dispense a medical fluid from the tube.

For example, the electrode can include a conductive tube covered by the insulator except at the end portion to form a conductive tip. It is also possible that the electrode includes a conductive coating or foil formed over a dielectric tube and covered by the insulator except at the end portion to form a conductive tip. Further, the electrode can include a conductive tip mounted on the end portion of the tube and the conductive connection includes a wire connected to the tip. The tip can include an internal spring contact to provide a releasable connection with the wire. The internal spring contact can engage a plug on a distal end of the wire. It is also possible that the wire includes a spring connector at a distal end to provide a releasable connection with the tip. The tip can include an internal thread and the wire can include a threaded portion to engage the internal thread to provide a releasable connection with the tip. The conductive connection can include a segmented wire disposed within an elastic sheath such that drawing the elastic sheath causes segments of the segmented wire to separate and releasing the elastic sheath causes the segments to reconnect. It is also possible that the electrode includes a conductive tip configured to engage a stopper ring formed at the end portion of the tube, where the stopper ring and the tip form the selectively closeable valve and the conductive connection including a wire connected to the tip. The hollow tube can include a second electrode separated from the electrode disposed at the first end portion, where the second electrode is connected to a second conductive connection configured to electrically couple to the second electrode to provide a voltage to the second electrode. Further, the electrode can include a plurality of wires extending from the end portion. The plurality of wires can be divided to form a plurality of electrodes. The selectively closeable valve can include at least one opening in the medical device. Further, the medical device can be configured to provide combined tumor treatment using two or more of: radio frequency ablation, brachytherapy, chemotherapy and electrochemotherapy, for example.

Also in accordance with the principles of the present invention, an instrument is provided for combined tumor treatment via brachytherapy and electrochemotherapy which includes a hollow tube configured for insertion of radioactive brachytherapy sources in a target volume. The hollow tube includes a first end portion having at least one conductor disposed at the first end portion and an insulator configured over a length of the tube such that conductive materials of the tube, except for the at least one conductor, are electrically isolated from an exterior surface the tube. A conductive connection is configured to electrically couple to the at least one conductor to provide a voltage to the at least one conductor to provide an electric field for electrochemotherapy. A selectively closeable valve is configured to dispense a medical fluid from the tube to the target volume during the electrochemotherapy to provide increased uptake in tissue due to electroporation.

For example, the conductor(s) can include a conductive tube covered by the insulator except at the end portion to form a conductive tip. It is also possible that the conductor(s) can include a conductive coating or foil formed over a dielectric tube and covered by the insulator except at the end portion to form a conductive tip. Further, the conductor(s) can include a conductive tip mounted on the end portion of the tube and the conductive connection can include a wire connected to the tip. The tip can include an internal spring contact to provide a releasable connection with the wire. The internal spring contact can engage a plug on a distal end of the wire. It is also possible that the wire includes a spring connector at a distal end to provide a releasable connection with the tip. The tip can include an internal thread and the wire can include a threaded portion to engage the internal thread to provide a releasable connection with the tip. The conductive connection can include a segmented wire disposed within an elastic sheath such that drawing the elastic sheath causes segments of the segmented wire to separate and releasing the elastic sheath causes the segments to reconnect. Further, the conductor(s) can include a conductive tip configured to engage a stopper ring formed at the end portion of the tube, where the stopper ring and the tip form the selectively closeable valve and the conductive connection includes a wire connected to the tip. The hollow tube can include a second electrode separated from the conductor(s) disposed at the first end portion, where the second electrode is connected to a second conductive connection configured to electrically couple to the second electrode to provide a second voltage to the second electrode. It is also possible that the conductor(s) can include a plurality of wires extending from the end portion. The selectively closeable valve can include at least one opening in the instrument. Further, the instrument can also include a treatment controller configured to coordinate brachytherapy and electrochemotherapy from a same deployed position of the instrument, for example.

Also in accordance with the principles of the present invention, a method is provided for combining treatment modes in an interventional therapy procedure, which method includes providing a medical device including a hollow tube having a first end portion having at least one conductor disposed at the first end portion and an insulator configured over a length of the tube such that conductive materials of the tube, except for the at least one conductor, are electrically isolated from an exterior surface the tube, a conductive connection configured to electrically couple to the at least one conductor to provide a voltage to the electrode, and a selectively closeable valve configured to dispense a medical fluid from the tube; positioning the medical device at a first position at or in a target volume in accordance with a plan; performing a first treatment mode using the medical device at the first position to treat the target volume; and performing a second treatment mode which is different from the first treatment mode using the medical device at the first position to treat the target volume.

For example, performing a first treatment mode can include creating an electric field at or in the first position by providing a voltage to the at least one conductor; and dispensing a medical fluid through the valve can be performed during electrochemotherapy to provide increased uptake in tissue due to electroporation to treat the target volume. Performing a second treatment mode can include inserting radioactive brachytherapy sources in the medical device at or in the first position to treat the target volume. The exemplary method can further include performing a third treatment mode at or in the first position to treat the target volume, for example.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

In accordance with the present principles, medical instruments are provided to perform a plurality of different treatments during a single intervention. In one embodiment, the medical instrument includes a catheter configured to concurrently perform electrochemotherapy and high dose rate (HDR) brachytherapy. Since both electrochemotherapy and HDR brachytherapy need objects to be brought into or near a tumor volume, a combination of these two forms of local cancer therapy is possible without increasing the level of invasiveness and may be performed within only a single interventional procedure.

Using electrochemotherapy in combination with other tumor therapies may need an additional interventional step to place a number of electrodes in or around the tumor. The present disclosure uses already placed brachytherapy catheters as electrodes, so that no additional intervention is needed. Electroporation of deep-seated tissue uses long electrically conducting needles which may cause problems in magnetic resonance (MR) scanners. In particular, MR image-guided insertion of the electrodes may be impeded. One embodiment circumvents this problem by permitting a metallic connection to be inserted after a catheter has been placed. In electrochemotherapy, the anticancer drugs can be delivered either locally or systemically. Local delivery may provide better results; however, if the tumor is situated deep inside the body, local delivery is complicated. The present catheters can act as a drug delivery device to ensure efficient local delivery.

In particularly useful embodiments, a catheter permits for combined tumor treatment via brachytherapy and electrochemotherapy. The catheter allows for insertion of radioactive brachytherapy sources and additionally comprises an electrode at the tip (or other location) including (removable) electrical connections to the outside to be supplied with a voltage. When two or more electrodes (catheters) are placed within or close to the tumor, the electrodes can be used to generate an electric field for electrochemotherapy (increased anticancer drug uptake due to electroporation of the cell membranes). Furthermore, the catheter can be used for local drug delivery. In this way, two very effective local tumor therapies may be combined within a single interventional procedure.

It should be understood that the present invention will be described in terms of catheter-like medical instruments; however, the teachings of the present invention are much broader and are applicable to any instrument. In some embodiments, the present principles are employed in treating or processing complex biological or mechanical systems. In particular, the present principles are applicable to internal treatment procedures of biological systems, procedures in most areas of the body such as the liver, prostate, cervix, etc.

The elements depicted in the figures may be implemented in various combinations of hardware and software and provide functions which may be combined in a single element or multiple elements. The functions of the various elements shown in the figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Figure 1:
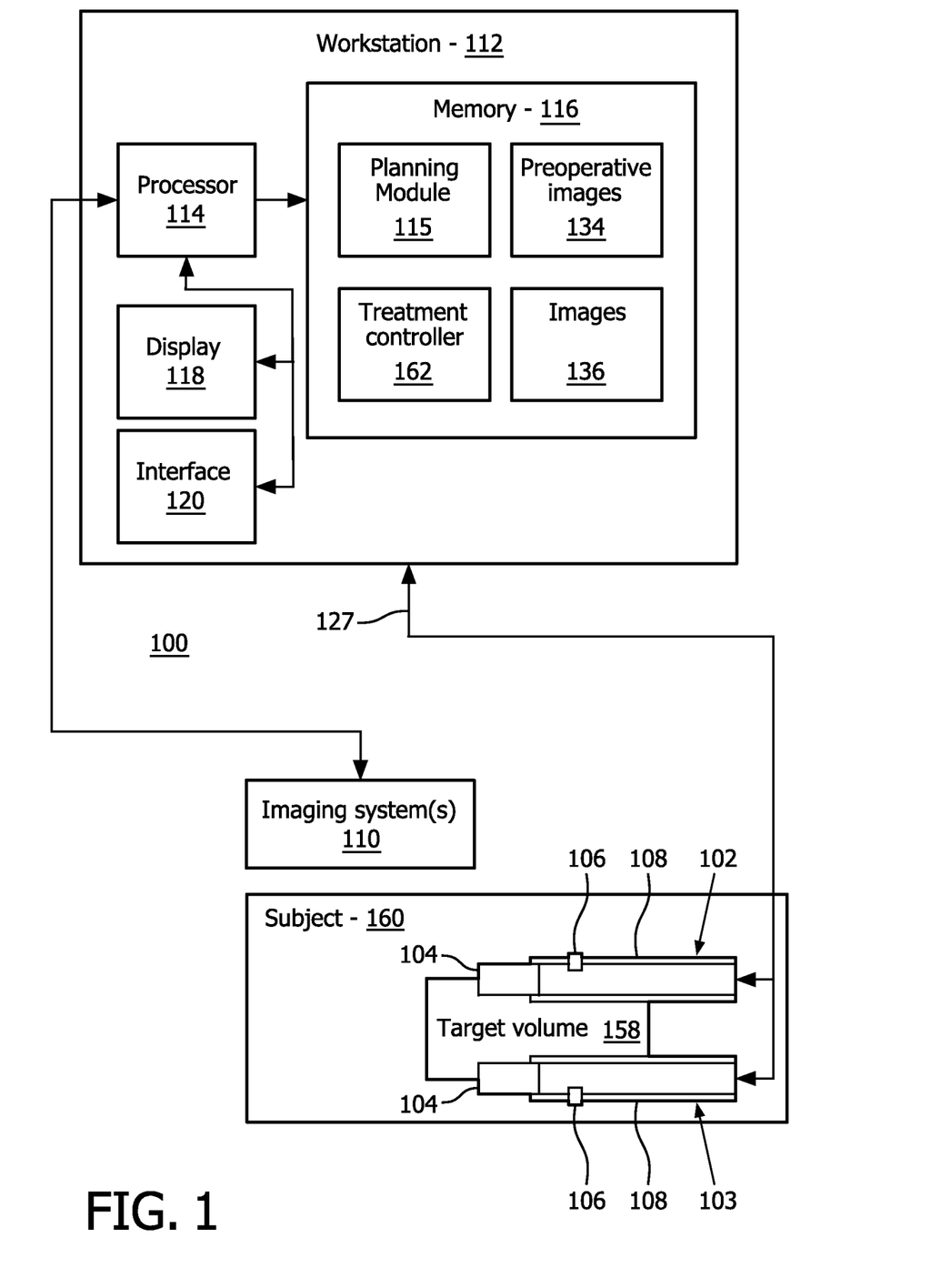
FIG. 1 is a block diagram showing a system for planning and executing multiple treatment therapies using a same medical instrument in accordance with the present principles.

Referring now to the drawings in which like numerals represent the same or similar elements and initially to FIG. 1, a planning and treatment system 100 is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a planning module (or algorithm) 115 configured to permit the placement and planning of brachytherapy therapy, electrochemotherapy, radio frequency ablation, chemotherapy, other therapy modes, etc. Planning module 115 may employ preoperative images 134 collected of a subject 160 in advance of a procedure. These preoperative images 134 may be employed along with real-time images 136 and other data collected during a procedure using imaging system(s) 110. The imaging system 110 may include an ultrasound system, X-ray system, MRI system, a computed tomography (CT) scanner, etc. One or more medical devices or instruments 102, 103 may be employed. The medical devices 102, 103 may include a catheter, a probe, an endoscope (with a channel), a robot, an electrode, a filter device, a balloon device, or other medical component, etc. The medical devices 102, 103 are configured to provide one or more different treatment types concurrently.

In one embodiment, the medical devices 102, 103 are configured with structures to provide for the application of an electric field and chemotherapy drugs for electrochemotherapy and are also configured to sequentially provide access paths for brachytherapy. For example, the devices 102 and 103 may include electrodes 104 for creating electrical fields and valves 106 for selectively releasing medical fluids in a subject 160. While two devices 102 and 103 are shown, each single device may be configured for both therapies. Two devices are depicted to provide two electrodes 104 for creating a distributed electric field for electroporation; however a single device may be equipped with two or more electrodes to create the distributed field, and the single device may be employed alone. One or both of the devices 102 and 103 may be configured in accordance with the present principles as will be further described below.

The devices 102, 103 connect to the workstation 112 through an electrical connection or cabling 127. The cabling 127 may include fiber optics, other electrical connections, channels, tubes and/or valves for dispensing liquids (e.g., medications, etc.), other instrumentation, etc., as needed. The devices 102, 103 may include a hollow tube structure with the electrodes 104 disposed on an exterior. The electrodes 104 are exposed to tissue while other portions of the devices 102 and 103 are coated or covered by an insulation material 108.

In one embodiment, workstation 112 includes a display 118 for viewing internal images of a subject (patient) 160 and/or a target volume 158 and may include overlay or other renderings to assist in locating and treating the target volume 158. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

In one embodiment, the medical device 102 includes a catheter which can be used as a brachytherapy applicator combined with the electrode 104 at a tip (or other location) of the catheter. The medical device 102 (catheter) includes an electrical connection to cabling 127 which continues outside the subject 160, and electrical insulation is included along the medical device 102. Different configurations and ways of connecting the electrode will be described below.

The planning module 115 may be employed to plan a first therapy treatment followed by a second therapy treatment using a same instrument 102 (and/or 103) and preferably in a same position for both therapies. Additional therapies may be added as well using the same instrument 102 (and position). For example, the present principles employ the same instrument 102 (e.g., catheter) for multiple treatment modes, such as, electrochemotherapy and HDR brachytherapy. Treatment planning for electrochemotherapy uses knowledge of exact electrode/instrument positions to optimize the electric field distribution and the voltages to be applied. When the catheter(s) (102) are concurrently or simultaneously used for HDR brachytherapy, this information is already available and treatment planning of the brachytherapy dose distribution and the electrochemotherapy field distribution are performed in a single step by the same software of the planning module 115.

In addition to planning, the workstation 112 is also equipped for executing the different modes of treatment. A treatment controller 162 is configured to control operations during a single interventional procedure to follow the plan stored in the planning module 115. Once the treatment plan is complete, brachytherapy and electrochemotherapy sessions can be performed independently from one another sequentially or concurrently as controlled by the controller 162. For example, an electrochemotherapy session can follow after each brachytherapy session or vice versa. The present principles can be applied to other tumor therapies as well which may combine, e.g., HDR brachytherapy (or any other local therapy employing (a set of) catheters) and treatments based on electroporation of the tumor cells (e.g., electrochemotherapy or irreversible electroporation).

Referring to FIGS. 2A-2F, different illustrative configurations are depicted showing construction of a hollow tube catheter equipped with a tip which may serve as an electrode or enables the presentation of an electrode. The configurations include an electrical connection from the electrode to a proximal end of the catheter, where a voltage source can be connected. The configurations provide a non-exhaustive list of embodiments for combined brachytherapy and electrochemotherapy catheters. Except for the electrode(s), the conductor is electrically insulated, so that only the electrode of the catheter is electrically connected to the surrounding tissue. Details of the configurations will be described as follows.

Figure 2A:
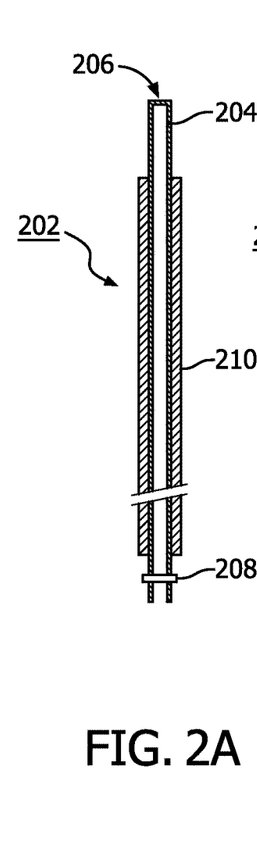
FIGS. 2A-2F show a plurality of configurations for a catheter configured to perform multiple therapies in accordance with illustrative embodiments.

Referring to FIG. 2A, a catheter 202 includes a conductor 204 that has an electrode forming a tip 206 and connects with an electrical connection 208 to the outside. The conductor 204 preferably includes a tube or may include a flexible conductor design (e.g., braided metal, stranded metal or the like). A non-conductive coating 210 is used as insulation around portions of the catheter 202, except for a small region at the tip 206 which serves as the electrode and a small region at the proximal end where a power supply cable can be connected.

Figure 2B:
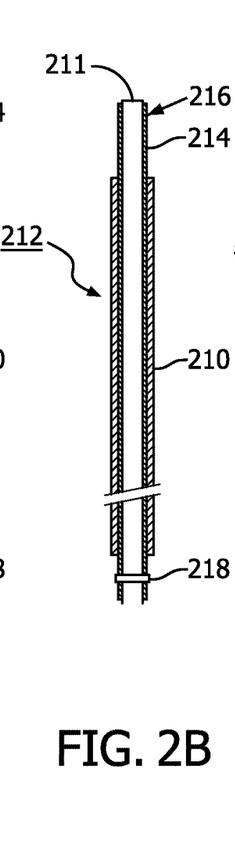

Referring to FIG. 2B, a catheter 212 is made of plastic or other polymeric material 211 and is supplied with a conductive coating 214 or a thin metal foil on the outside. Again, an additional non-conductive coating 210 insulates the surface from the outside, except for a tip 216 and an external connection region 218.

Figure 2C:
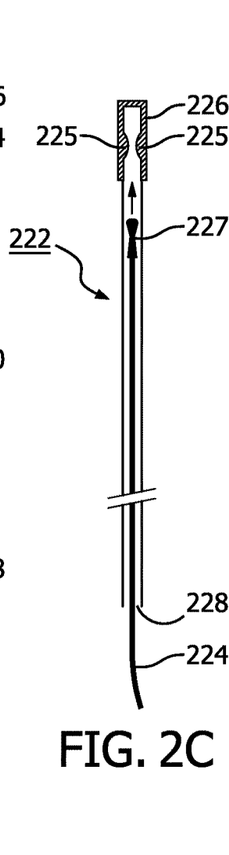

Referring to FIG. 2C, a catheter 222 is made of plastic or other flexible polymeric material with a conductive tip 226 which serves as an electrode. The tip 226 is connected with a wire 224 which can be inserted through a lumen 228 of the catheter 222 from the outside when the catheter is already in place. Good electrical connection is ensured by a spring contact 225 inside the tip 226. The spring contact 225 engages a plug 227 or other structure to secure the wire 224 and make (or break) the electrical connection therebetween. The wire 224 can easily be removed after electrochemotherapy treatment to make room for a radioactive source of the brachytherapy session which follows. Since there is no permanent metallic connection along the catheter, this device is MR-safe and can be made from highly flexible materials.

Figure 2D:
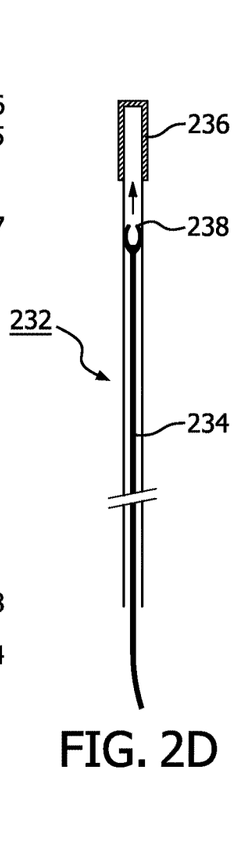

Referring to FIG. 2D, this embodiment is similar to the embodiment described in FIG. 2C, except for the contact between the tip and wire. A catheter 232 includes a tip 236 that has a flat inner surface while a wire 234 is equipped with a spring connector 238. The spring connector 238 may include a horse-shoe shape or other spring shape to engage opposite interior sides of the tip 236. This has the advantage that a brachytherapy source can easily be slid all the way through the catheter 232 and through the tip 236 without getting stuck within a spring contact, as may be a concern in the embodiment in FIG. 2C. The catheter 232 still permits selective securing (or releasing) of the spring connector 238 to/from the tip 236 to make or break electrical contact for electrochemotherapy applications.

Figure 2E:
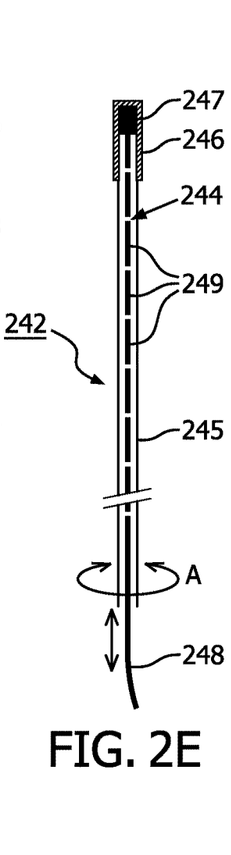

Referring to FIG. 2E, another catheter 242 employs an electrical wire 244 feed through a dielectric tube 245. The wire 244 includes a threaded tip portion 247 that engages an inner surface of a conductive tip 246. The conductive tip 246 may be connected to the catheter's metal tip after insertion via a threaded connection by applying a rotating motion (arrow "A"). In one embodiment, the wire 244 is segmented inside an elastic sheath or coating 248. Segments 249 of the wire 244 may be connected in a free state and disconnected by pulling or stretching the elastic sheath 248 from a proximal end. Spaces between segments 249 are useful for visualization during MR imaging. The wire 244 can be completely removed after unscrewing/releasing it from the tip portion 246.

Figure 2F:
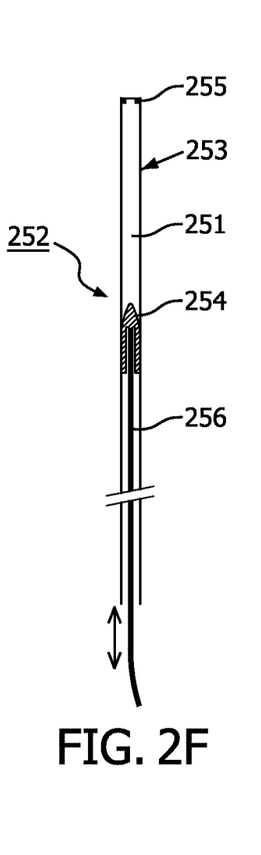

Referring to FIG. 2F, a catheter 252 includes at least one lumen 251 open at a tip portion 253 permitting placement of a conductive wire tip 254 of a conductive wire 256 therein to seal the lumen 251 or for opening the lumen 251 permitting local administration of drugs. Employing a piston principle the catheter 252 includes an end portion configured to receive and be sealed off when in contact with the tip 254 to avoid fluid leakage and possibly to inject fluid drugs, assuming that the wire 256 is rigid enough. To prevent the conductive wire tip 254 (or other devices inserted into the catheter) from sliding out of the distal end, a stopper ring 255 is incorporated into the catheter's end portion. A non-conductive wire/tip (a plug) may be inserted to prevent leakage, etc. during pauses.

The catheter types of FIGS. 2A-2F may have an opening at the tip so that they can be pulled over a guide wire for insertion. This opening needs to be closed with a plug when the catheter is in place to prevent liquids from entering the catheter. Gamma rays emitted by HDR brachytherapy sources will be attenuated by any metal parts of the catheter. This attenuation can be measured or calculated depending on the position of the source in the catheter and needs to be considered by the brachytherapy treatment planning algorithm or module. In addition, a second electrode may be employed further down the shaft of the catheter to produce an electric field in the tissue for electroporation or other processes. In addition, a second electrode may be provided externally to the subject to provide the electric field or by employing an additional catheter or other devices with another electrode. Embodiments in FIGS. 2C-2F are particularly useful for MR-safe insertion of electroporation electrodes, allowing for MR image-guided electrode placement in deep-seated regions of the body.

Figure 3:
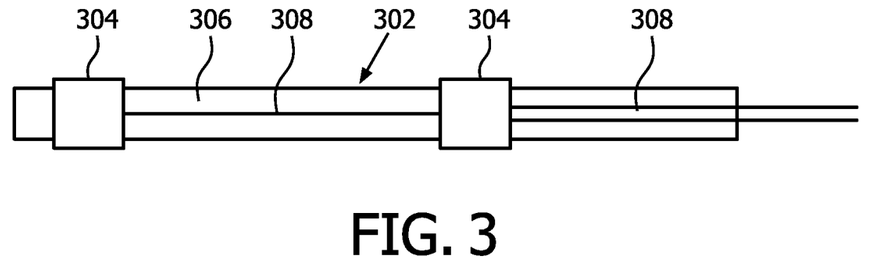
FIG. 3 is a perspective view showing another embodiment employing two or more electrodes along a same catheter which can be connected separately for generating a distributed electric field in accordance with illustrative embodiments.

Referring to FIG. 3, another embodiment employs two or more electrodes 304 along a catheter 302, which can be connected separately, e.g., through separate conducting metal strips or coatings 308 on a catheter surface 306 (or internally). This permits better control of the electric field distribution in space.

Figure 4:
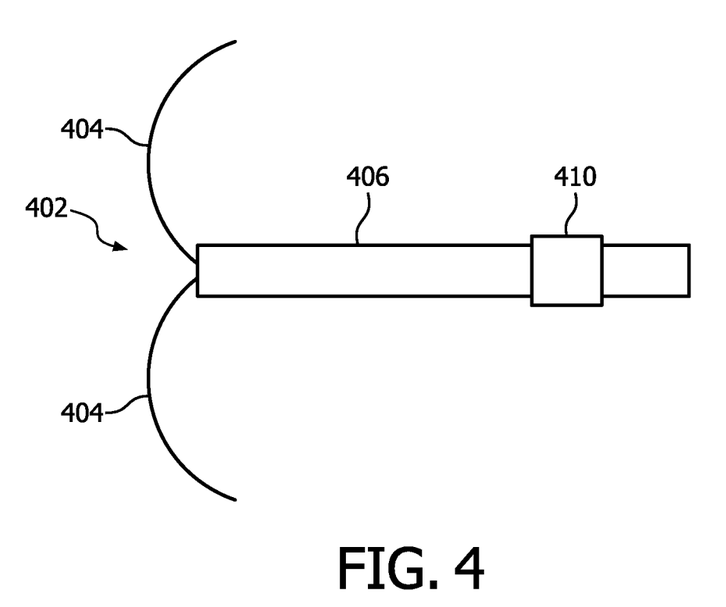
FIG. 4 is a perspective view showing an umbrella configuration for a tip electrode in accordance with one illustrative embodiment.

Referring to FIG. 4, an umbrella-shaped electrode 402 may be employed which is similar to those employed in radio-frequency ablation (RFA). Umbrella wires 404 are pushed through a catheter 406 and automatically bend to form the umbrella shape. The umbrella wires 404 may include any number and may be oriented in any useful configuration. The electrode 402 could be combined with a second electrode 410 further down the shaft of the catheter 406 to produce an electric field for electroporation within a large volume. The umbrella wires 404 may be divided into groups or subsets and employed as separate electrodes.

Figure 5:
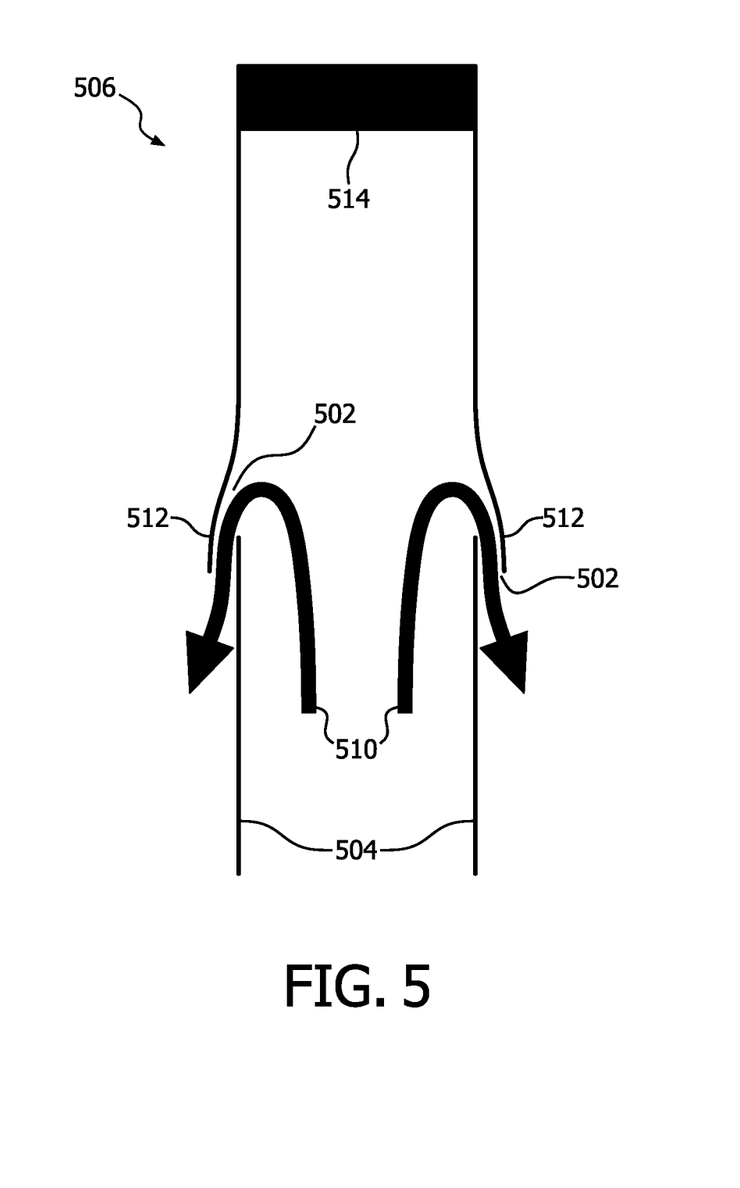
FIG. 5 is a diagram showing a selectively closable valve for dispensing fluids in accordance with one illustrative embodiment.

Referring to FIG. 5, in another embodiment, one or several openings 502 on catheter walls 504 near a distal tip of a catheter 506 permit local delivery of fluids 510, such as medication, treatment solutions or drugs (e.g., anticancer drugs for electrochemotherapy, etc.). The openings 502 include a valve 512 or other closable structure to selectively enable or prevent fluid flow to/from the catheter 506. The openings 502 may be secured by small valves formed, e.g., from a plastic or rubber lid. The valves 512 may be actuated by servos, wires or other mechanical devices. The tube formed by the catheter 506 may be plugged by a plug 514 or other structure to close of the end portion.

The embodiments described and shown in FIGS. 2-5 are particularly useful for treatment of cancer, and more specifically for applying multiple different treatment types in a same interventional procedure.

Figure 6:
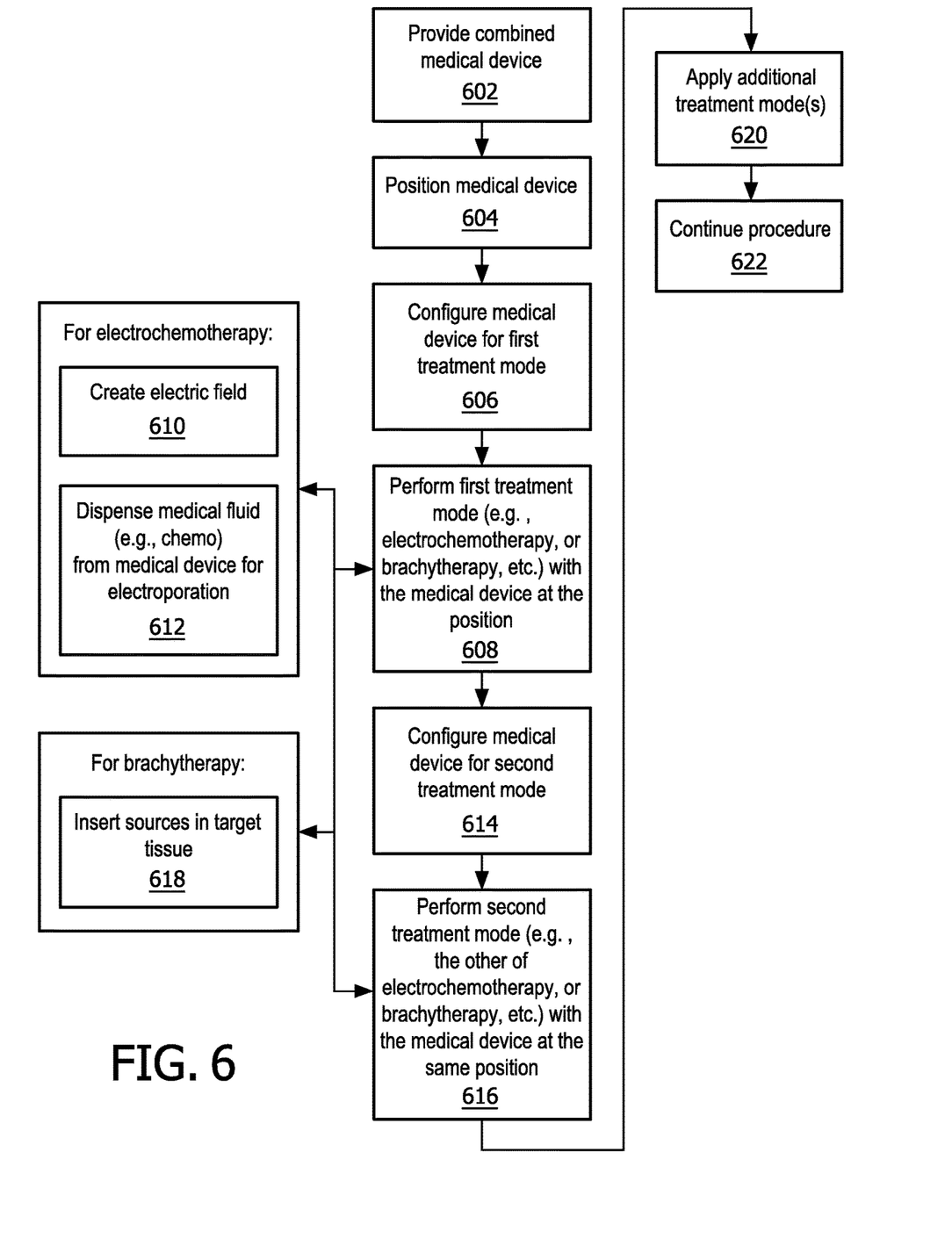
FIG. 6 is a block/flow diagram showing a method for combining treatment modes in a single interventional therapy procedure in accordance with illustrative embodiments.

Referring to FIG. 6, a method for combining treatment modes in an interventional therapy procedure is illustratively shown. In block 602, a medical device, such as a catheter is provided. The medical devices includes a hollow flexible or rigid tube having a first end portion having at least one conductor with an electrode(s) disposed at the first end portion and an insulator configured over a length of the tube such that conductive materials of the tube except for the electrode(s) are electrically isolated from an exterior surface the tube. A conductive connection is configured to electrically couple to the at least one conductor to provide a voltage to the electrode, and a selectively closeable valve may be provided and configured to dispense a medical fluid from the tube. The medical device may be provided in a plurality of configurations, as shown and described, e.g., in FIGS. 2A-2F, 3, 4 and 5. In block 604, the medical device is positioned in a subject at a first position at or in a target volume in accordance with a plan. The plan is generated in advance by known methods.

In block 606, the medical device may be configured for performing a first treatment mode. This may include inserting or removing a conductive wire, securing or releasing the conductive wire, opening or closing the valve, applying an electric field, deploying conductive wires from a tip of the device, etc. In block 608, the first treatment mode is performed using the medical device at the first position to treat the target volume. The first treatment mode may include brachytherapy, chemotherapy, electrochemotherapy, etc.

In block 610, one example of performing the first treatment mode includes creating an electric field in target tissue at or in the first position by providing a voltage to the electrode, and dispensing a medical fluid through the valve during electrochemotherapy to provide increased uptake in tissue due to electroporation to treat the target volume in block 612.

In block 614, the medical device is configured for performing a second treatment mode. This may include inserting or removing a conductive wire, securing or releasing the conductive wire, opening or closing the valve, applying an electric field, deploying conductive wires from a tip of the device, etc. In block 616, the second treatment mode is performed (which is different from the first treatment mode) using the medical device at the first position to treat the target volume. The second treatment mode may include brachytherapy, chemotherapy, electrochemotherapy, etc. but not the same mode as the first treatment mode. In block 618, one example of performing a second treatment mode includes inserting radioactive brachytherapy sources in the medical device at or in the first position to treat the target volume. It should be understood that the first and second modes of treatment may be applied in reverse order. Other configurations and steps may be employed as well, for example, multiple catheters with electrodes may be employed to form a larger or well-defined electrical field or multiple catheters may be employed to locate multiple HDR brachytherapy sources, etc.

In block 620, a third treatment mode (or more) may be performed at or in the first position to further treat the target volume. In block 622, the procedure continues until the plan is carried out and/or target volume is completely treated.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for combined brachytherapy and electrochemotherapy catheters (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical device for multiple treatment therapies, comprising:
  a hollow tube having a first end portion which comprises an electrode and an insulator configured over a length of the tube such that conductive materials of the tube except for the electrode are electrically isolated from an exterior surface of the tube;
  a conductive connection configured to electrically couple to the electrode to provide a voltage thereto, said conductive connection configured to be releasably inserted into the hollow tube while the hollow tube is positioned at an internal treatment site, wherein the conductive connection is configured to contact the electrode and electrically couple to the electrode while the hollow tube is positioned at the internal treatment site; and
  a selectively closeable valve configured to dispense a medical fluid from the tube.

2. The medical device as recited in claim 1, wherein at least one of (i) the electrode includes a conductive tube covered by the insulator except at the end portion to form a conductive tip, or (ii) the electrode includes a conductive coating or foil formed over a dielectric tube and covered by the insulator except at the end portion to form a conductive tip.

3. The medical device as recited in claim 1, wherein the electrode includes a conductive tip mounted on the end portion of the tube and the conductive connection includes a wire connected to the tip.

4. The medical device as recited in claim 3, wherein the tip includes an internal spring contact to provide a releasable connection with the wire.

5. The medical device as recited in claim 4, wherein the internal spring contact engages a plug on a distal end of the wire.

6. The medical device as recited in claim 3, wherein the wire includes a spring connector at a distal end to provide a releasable connection with the tip.

7. The medical device as recited in claim 3, wherein the tip includes an internal thread and the wire includes a threaded portion to engage the internal thread to provide a releasable connection with the tip.

8. The medical device as recited in claim 1, wherein the conductive connection includes a segmented wire disposed within an elastic sheath such that drawing the elastic sheath causes segments of the segmented wire to separate and releasing the elastic sheath causes the segments to reconnect.

9. The medical device as recited in claim 1, wherein the electrode includes a conductive tip configured to engage a stopper ring formed at the end portion of the tube, the stopper ring and the tip forming the selectively closeable valve and the conductive connection including a wire connected to the tip.

10. The medical device as recited in claim 1, wherein the hollow tube includes a second electrode separated from the electrode disposed at the first end portion, the second electrode being connected to a second conductive connection configured to electrically couple to the second electrode to provide a voltage to the second electrode.

11. The medical device as recited in claim 1, wherein the electrode includes a plurality of wires extending from the end portion, and wherein the plurality of wires are divided to form a plurality of electrodes.

12. The medical device as recited in claim 1, wherein the selectively closeable valve includes at least one opening in the medical device.

13. The medical device as recited in claim 1, wherein the medical device is configured to provide combined tumor treatment using two or more of: radio frequency ablation, brachytherapy, chemotherapy and electrochemotherapy.

14. An instrument for combined tumor treatment via brachytherapy and electrochemotherapy, comprising:
   a hollow tube configured for insertion of radioactive brachytherapy sources in a target volume, the hollow tube including a first end portion having at least one conductor disposed at the first end portion and an insulator configured over a length of the tube such that conductive materials of the tube, except for the at least one conductor, are electrically isolated from an exterior surface the tube,
   a conductive connection configured to electrically couple to the at least one conductor to provide a voltage to the at least one conductor to provide an electric field for electrochemotherapy, said conductive connection configured to be releasably inserted into the hollow tube while the hollow tube is positioned at an internal treatment site, wherein the conductive connection is configured to contact the electrode and electrically couple to the electrode while the hollow tube is positioned at the internal treatment site; and
   a selectively closeable valve configured to dispense a medical fluid from the tube to the target volume during the electrochemotherapy to provide increased uptake in tissue due to electroporation.

15. A method for combining treatment modes in an interventional therapy procedure, comprising:
   providing a medical device including a hollow tube having a first end portion having at least one conductor disposed at the first end portion and an insulator configured over a length of the tube such that conductive materials of the tube, except for the at least one conductor, are electrically isolated from an exterior surface the tube, a conductive connection configured to electrically couple to the at least one conductor to provide a voltage to an electrode, said conductive connection configured to be releasably inserted into the hollow tube while the hollow tube is positioned at an internal treatment site, wherein the conductive connection is configured to contact the electrode and electrically couple to the electrode while the hollow tube is positioned at the internal treatment site, and a selectively closeable valve configured to dispense a medical fluid from the tube;
   positioning the medical device at a first position at or in a target volume in accordance with a plan; performing a first treatment mode using the medical device at the first position to treat the target volume; and
   performing a second treatment mode which is different from the first treatment mode using the medical device at the first position to treat the target volume.

* * * * *